United States Patent
Escandon et al.

(10) Patent No.: US 7,015,253 B2
(45) Date of Patent: Mar. 21, 2006

(54) REGIMEN FOR TREATING PROSTATE TISSUE AND SURGICAL KIT FOR USE IN THE REGIMEN

(75) Inventors: M. Alejandro Sousa Escandon, Lugo (ES); Johann J. Neisz, Minnetonka, MN (US)

(73) Assignee: American Medical Systems, Inc., Minnetonka, MN (US)

( * ) Notice: Subject to any disclaimer, the term of this patent is extended or adjusted under 35 U.S.C. 154(b) by 127 days.

(21) Appl. No.: 10/193,716

(22) Filed: Jul. 9, 2002

(65) Prior Publication Data

US 2003/0092689 A1 May 15, 2003

Related U.S. Application Data

(60) Provisional application No. 60/304,149, filed on Jul. 10, 2001, provisional application No. 60/329,262, filed on Oct. 12, 2001.

(51) Int. Cl.
*A01N 31/00* (2006.01)
*A61K 31/45* (2006.01)

(52) U.S. Cl. .......................... 514/724; 514/874; 600/7
(58) Field of Classification Search .................. 600/29, 600/31, 7; 604/264, 523, 528; 514/874, 514/724
See application file for complete search history.

(56) References Cited

U.S. PATENT DOCUMENTS

| | | | |
|---|---|---|---|
| 3,847,988 A | 11/1974 | Gold | |
| 3,875,229 A | 4/1975 | Gold | |
| 4,097,578 A | 6/1978 | Perronnet et al. | |
| 4,220,735 A | 9/1980 | Dieck et al. | |
| 4,239,776 A | 12/1980 | Glen et al. | |
| 4,377,584 A | 3/1983 | Rasmusson et al. | |
| 4,386,080 A | 5/1983 | Crossley et al. | |
| 4,461,283 A | 7/1984 | Doi | |
| 4,636,505 A | 1/1987 | Tucker | |
| 4,760,071 A | 7/1988 | Rasmusson et al. | |

(Continued)

FOREIGN PATENT DOCUMENTS

WO    WO 92/10142    6/1992

(Continued)

OTHER PUBLICATIONS

Zeneca Pharmaceuticals, Professional Information Brochure for Casodex Bicalutamide Tablets, Sep. 2000, 2 pages.

(Continued)

*Primary Examiner*—Christopher S. F. Low
*Assistant Examiner*—Amy Lewis
(74) *Attorney, Agent, or Firm*—Faegre & Benson LLP

(57) ABSTRACT

The present invention provides treatment regimens for treating diseased prostate tissue, including the steps of chemically ablating prostate tissue and coadministering an antiandrogen. In some embodiments, prostate tissue is chemically ablated by injection of ethanol, or an injectable gel comprising ethanol, into prostate tissue. Steroidal and non-steroidal antiandrogens are suitable antiandrogens. One suitable non-steroidal antiandrogen is bicalutamide. The treatment regimen is suitable for treatment of prostate tissue diseases including benign prostatic hyperplasia and prostatic carcinoma. The invention further provides a treatment regimen for treating benign prostatic hyperplasia, including the steps of damaging prostate tissue and coadministering an antiandrogen. Also provided by the present invention is a kit for treating a human male, including a means for necrosing prostate tissue, an antiandrogen drug, and a means for administering the antiandrogen drug. A kit including a first surgical device for delivering a chemoablation fluid to prostate tissue transurethrally, an antiandrogen drug such as bicalutamide, and a second surgical device for administering the antiandrogen drug, is further provided.

40 Claims, 3 Drawing Sheets

U.S. PATENT DOCUMENTS

| | | | |
|---|---|---|---|
| 5,116,615 | A | 5/1992 | Gokcen et al. |
| 5,322,503 | A | 6/1994 | Desai |
| 5,562,703 | A | 10/1996 | Desai |
| 5,630,794 | A | 5/1997 | Lax et al. |
| 5,672,171 | A | 9/1997 | Andrus et al. |
| 5,753,641 | A | 5/1998 | Gormley et al. |
| 5,770,603 | A | 6/1998 | Gibson |
| 5,817,649 | A * | 10/1998 | Labrie ........................ 514/169 |
| 5,861,002 | A | 1/1999 | Desai |
| 5,872,150 | A | 2/1999 | Elbrecht et al. |
| 5,994,362 | A | 11/1999 | Gormley et al. |
| 6,022,860 | A | 2/2000 | Engel et al. |
| 6,142,991 | A | 11/2000 | Schatzberger |
| 6,179,831 | B1 | 1/2001 | Bliweis |
| 6,200,573 | B1 | 3/2001 | Locke |
| 6,217,860 | B1 | 4/2001 | Woo et al. |
| 6,231,591 | B1 | 5/2001 | Desai |
| 6,378,525 | B1 | 4/2002 | Beyar et al. |
| 2001/0048942 | A1 | 12/2001 | Weisman et al. |
| 2002/0040220 | A1 | 4/2002 | Zvuloni et al. |

FOREIGN PATENT DOCUMENTS

| | | |
|---|---|---|
| WO | WO 93/15664 | 8/1993 |

OTHER PUBLICATIONS

Zeneca Pharmaceuticals, Professional Information Brochure for Zoladex Goserelin Acetate Implant—3-Month, Feb. 1999, 2 pages.

Zeneca Pharmaceuticals, Professional Information Brochure for Zoladex Goserelin Acetate Implant—3.6mg, Feb. 1999, 2 pages.

http://www.cancerbacup.org.uk/info/flutamide.html, CancerBACUP, "Flutamide (Drogenil)", downloaded Jun. 25, 2001, 3 pages.

http://www.rxmed.com, RxMed, "Anandron", downloaded Jun. 25, 2001, 4 pages.

http://www.phc.vcu.edu/feature/finasteride/finasteride.html, Schieck, Cynthia L., Finasteride (Propecia), downloaded May 31, 2002, 6 pages.

http://www.merck.com/product/usa/proscar/hcp/prod_att/specificity.html?US_healthcare=yes, Merck & Co., Inc. "DHT Hormone Information at Proscar.com", downloaded Jun. 5, 2002, 2 pages.

www.merck.com, Merck & Co., Inc., "Physician Prescribing Information—Proscar (Finasteride) Tablets", downloaded Jun. 25, 2001, 2 pages.

Zincke, Horst et al., "Role of Early Adjuvant Hormonal Therapy After Radical Prostatectomy for Prostate Cancer", The Journal of Urology, vol. 166, pp. 2208-2215, Dec. 2001.

"The Management of Radiation Failure in Prostate Cancer", Reviews in Urology, vol. 4, supplement 2, 2002, 35 pages.

"Cryoablation of the Prostate", Urology, vol. 60, Supplement 2A, Aug. 2002, 58 pages.

Zippe, Craig D., "Cyrosurgery of the Prostate—Techniques and Pitfalls", The Craft of Urologic Surgery, from the Prostate Center, Department of Urology, Cleaveland Clinic Foundation, Cleveland, Ohio, Urologic Clinics of North America, vol. 23, No. 1, Feb. 1996, pp. 147-163.

P. Derakshani et al., "Cryoablation of Localized Prostate Cancer", European Urology, vol. 34, pp. 181-187, 1998.

Arie Belldegrun et al, "Society of Urologic Oncology Biotechnology Forum: New Approaches and Targets for Advanced Prostate Cancer", The Journal of Urology, Oct. 2001, vol. 166: pp. 1316-1321.

Terry Cook et al, "Development of GnRH Antagonists for Prostate Cancer: New Approaches to Treatment", The Oncologist 2000, vol. 5: pp. 162-168.

John Trachtenberg et al, "A Phase 3, Multicenter, Open Label, Randomized Study of Abarelix Versus Leuprolide Plus Daily Antiandrogen in Men with Prostate Cancer", The Journal of Urology, Apr. 2002, vol. 167: pp. 1670-1674.

Hans J. Stricker, "Luteinizing Hormone-Releasing Hormone Antagonists in Prostate Cancer", Elsevier Science Inc., Urology 58: (Supplement 2A), Aug. 2001, pp. 24-27.

Peter Zvara et al, "Ablation of Canine Prostate Using Transurethral Intraprostatic Absolute Ethanol Injection", Elsevier Science Inc., Urology 54 (3) 1999, pp. 411-415.

Peter Zvara et al, "Ablation of Canine Prostate Using Transurethral Intraprostatic Absolute Ethanol Injection", Department of Surgery, Division of Urology and Department of Pathology, University of Vermont College of Medicine, dated prior to Jul. 9, 2002, pp. 1-15.

Peter Zvara, M.D., Ph. D. et al, "Ablation of Canine Prostate Using Transurethral Intraprostatic Absolute Ethanol Injection", Department of Surgery, Division of Urology and Department of Pathology* University of Vermont College of Medicine, www.injectTx.com., 2 pages.

Nobuyuki Goya et al, "Ethanol Injection Therapy of the Prostrate for Benign Prostatic Hyperplasia: Preliminary Report on Application of a New Technique", The Journal of Urology, Aug. 1999, vol. 162: pp. 383-386.

David A. Levy et al, "Transrectal Ultrasound-Guided Intraprostatic Injection of Absolute Ethanol With and Without Carmustine: A Feasibility Study in the Canine Model", Elsevier Science Inc, Urology 53, 1999, 7 pages.

Peter J. Littrup, M.D. et al, "Percutaneous Ablation of Canine Prostate Using Transrectal Ultrasound Guidance-Absolute Ethanol and Nd:YAG Laser", Investigative Radiology, Oct. 1988, vol. 23. pp. 734-739.

Tito Livraghi, M.D. et al, "Long Term Results of Single Session Precutaneous Ethanol Injection in Patients with Large Hepatocellular Carcinoma", American Cancer Society, Jul. 1998, Cancer, vol. 83(1): pp. 48-57.

Y. Iso et al, "Repeated Injection Selerotherapy is Preferable to Combined Therapy with Variceal Ligation to Avoid Recurrence of Esophageal Varices: A Prospective Randomized Trial", Hepato-Gastroenterology, (1997), vol. 44: pp. 467-471.

Tito Livraghi, M.D. et al, "Small Hepatocellular Carcinoma: Percutaneous Alcohol Injection-Results in 23 Patients", Radiology, Aug. 1988, vol. 168 (2): pp. 313-317.

T. Fujisawa et al, "Intratumoral Ethanol Injection for Malignant Tracheobronchial Lesions: A New Broncofiberscopic Procedure", Endoscopy, 1986, vol. 18: pp. 188-191.

Tito Livraghi, M.D. et al, "US-guided Percutaneous Alcohol Injection of Small Hepatic and Abdominal Tumors", Radiology, Nov. 1986, vol. 161 (2): pp. 309-312.

Francis A. Burgener, M.D. et al, "Treatment of Experimental Adenocarcinomas by Percutaneous Intratumoral Injection of Absolute Ethonal", Investigative Radiology, Jun. 1987, vol. 22 (6): pp. 472-475 & 477-478.

R. Uflacker et al, "Ablation of Tumor and Inflammatory Tissue With Absolute Ethanol", Acta Radiologica Diagnosis 27 (1986), Fasc.: 2, pp. 131-138.

Luigi Solbiati, M.D. et al, "Percutaneous Ethanol Injection of Parathyroid Tumors under US Guidance: Treatment for Secondary Hyperparathyroidism[1]", Radiology, Jun. 1985, vol. 155 (3): pp. 607-610.

A. Giangrande et al, "Ultrasonically Guided Fine-Needle Alcohol Injection as an Adjunct to Medical Treatment in Secondary Hyperparathyroidism", Proc EDTA-ERA (1984), vol. 21: pp. 895-901.

Eldon Olson et al, "Transrenal-Vein Reflux Ethanol Sclerosis of Gastroesophagel Varices", AJR, Sep. 1984, vol. 143: pp. 627-628.

H.J. Teerstra et al, "Ethanol Embolization of a Renal Tumor, Complicated by Colonic Infarction", Diagn. Imag. Clin. Med., 1984, vol. 53: pp. 250-254.

William J. Bean, M.D., "Renal Cysts: Treatment with Alcohol", Diagnostic Radiology, Feb. 1981, vol. 138: pp. 329-331.

Jordan Katz, M.D. et al, "Treatment of Diffuse Metastatic Cancer Pain by Instillation of Alcohol into the Sella Turcica", Anesthesiology, Feb. 1977, vol. 46 (2): pp. 115-119.

Thomas M. Tank, M.D. et al, "Intrathecal Injections of Alcohol or Phenol for Relief of Intractable Pain", Cleveland Clinic Quaterly, Jul. 1963, vol. 30: pp. 111 & 116-117.

Leonard J. T. Murphy, M. S., F.R.A.C.S., F.A.C.S., excerpt from "The Prostate", *The History of Urology*, 1972, pp. 385 and 442-452.

Michael F. Darson, M.D. et al, "Transurethral Enzyme Injection—Future Management of Benign Prostatic Hyperplasia", Mayo Clin Proc, Sep. 1998, vol. 73: pp. 908-911.

William J. Harmon et al, "Transurethral Enzymatic Ablation of the Prostate: Canine Model", Elsevier Science Inc., 1996, Urology, vol. 48: pp. 229-232.

A. Choudhury et al, "Evaluation of the Role of Injection Therapy for Benign Prostatic Hypertrophy", British Journal of Urology, 1980, vol. 52: pp. 204-207.

M. Bhargava et al, "Experimental Evaluation of Injection Therapy of Enlarged Prostate: Part I—Histopathological Changes Induced by Intra-Prostatic Injection of Carbolic Acid-Acetic Acid-Glycerine Mixture", Indian Journal of Experimental Biology, Sep. 1977, vol. 15: pp. 762-767.

S. G. Kagra et al, "Experimental Evaluation of Injection Therapy of Enlarged Prostate: Part II—Fate of the Fluid Injected", Indian Journal of Experimental Biology, Sep. 1977, vol. 15: pp. 768-771.

J. Jhanwar et al, "Experimental Evaluation of Injection Therapy of Enlarged Prostate: Part III—Effect of Carbolic Acid-Acetic Acid-Glycerine Mixture on Vessels", Indian Journal of Experimental Biology, Sep. 1977, vol. 15: pp. 772-775.

G. D. Sharma et al, "Transperineal Intraprostatic Injection Treatment of Benign Prostatic Enlargement", Aust. N.Z. J. Surg., Apr. 1977, vol. 47 (2): pp. 220-222.

Hussein Bin Mahamed Salleh, "The Treatment of Benign Prostatomegaly by Injection" Aust. N.Z. J. Surg., Dec. 1973, vol. 43(3): pp. 278-280.

A.C. Broughton et al, "The Significance of Perineal Pain After Injection of the Prostate", British Journal of Urology, 1970, vol. 42: pp. 73 & 75.

E. J. G. Milroy, FRCS, "Prostatic Injection", Nursing Times, May 1969, pp. 652-653.

J. C. Angell, F.R.C.S., "Treatment of Benign Prostatic Hyperplasia by Phenol Injection", British Journal of Urology, 1969, vol. 41: pp. 735-738.

E. J. G. Milroy, "Treatment of the Enlarged Benign Prostate Using Local Injection: A Preliminary Report", W.I. Med. J., 1968, vol. XVII: pp. 241-245.

B. Reddington, SRN, "Retention of Urine due to Simple Prostatic Enlargement-Treatment by Prostatic Injection", Nursing Times, Aug. ??, 2 pages.

A.N. Akilie, "Treatment by Prostatic Injection of Acute Urinary Retention due to Prostatic Hyperplasia", British Medical Journal, 1967, vol. 2: pp. 418-419.

G. L. Talwar, "Injection Treatment of Enlarged Prostate", Brit. J. Surg., May 1966, vol. 53 (5): pp. 421-427.

L. Baert, M.D. et al, "Treatment of Chronic Bacterial Prostatitis by Local Injection of Antibiotics into Prostate", Urology, Apr. 1983, vol. 21: pp. 370-375.

W. E. Hatch, "Intraprostatic Injection of Penicillin", The Journal of Urology, Dec. 1950, vol. 64 (6): pp. 763-766.

M. R. G. Robinson et al, "Adjuvant Immunotherapy with B. C. G. in Carcinoma of the Prostate", British Journal of Urology, 1977, vol. 49: pp. 221-226.

R. H. Flocks, M. D., Interstitial Irradiation Therapy With a Solution of $Au^{198}$ as Part of Combination Therapy for Prostatic Carcinoma$^{1,2}$, Journal of Nuclear Medicine, 1964, vol. 5: pp. 691-705.

Frank E. Ceccarelli et al, Technique of Radical Retropubic Prostato-Seminal Vesiculectomy and Injection of $AU^{198}$, The Journal of Urology, Jun. 1962, vol. 87 (6), pp. 951-963.

George J. Bulkley et al, "Treatment of Carcinoma of the Prostate by Interstitial Irradiation with Radioactive Gold", Experimental and Clinical Studies, pp. 126-127 & 130-133.

John A. D. Cooper et al, "Intraprostatic Injection of Radioactive Colloids. I. Distribution and Excretion Following Injection in the Dog", The Journal of Urology, May 1954, vol. 71 (5): pp. 624-627.

Hiroyuki Amano, "Ethanol Injection Therapy for Locally Invasive Prostatic Adenocarcinoma", Elsevier Science Inc., Urology 59 (5) 2002, pp. 771-772.

T. Battmann, "Pharmacological Profile of RU 58642, a Potent Systemic Antiandrogen foe the Treatmetn of Androgen-dependent Disorders", J. Steroid Biochem. Molec. Biol., vol. 64,(1/2), pp. 103-111, 1998.

Jean Wilson, "The Testes and The Prostate—A Continuing Relationship", The New England Journal of Medicine, vol. 317, Sep. 3, 1987, 628-629.

E. di Salle et al, "PNU 157706, a Novel Dual Type I and II 5α-Reductase Inhibitor", J. Steroid Biochem. Molec. Biol., Bol. 64(3-4) 1998, pp. 179-186.

Neil E. Fleshner et al, "Combination Finasteride and Flutamide in Advanced Carcinoma of the Prostate: Effective Therapy with Minimal Side Effects", The Journal of Urology, vol. 154, Nov. 1995, pp. 1642-1646.

Nobuyuki Goya, "Ethanol Injection Therapy of the Prostate for Benign Prostatic Hyperplasia: Preliminary Report on Application of a New Technique", Journal of Urology, vol. 162(8), Aug. 1999, pp. 383-386.

Gianfraco Savoca et al., "Percutaneous Ethanol Injection of the Prostate as Minimally Invasive Treatment for Benign Prostatic Hyperplasia: Preliminary Report", European Urology, vol. 40, 2001, pp. 504-508.

Tito Livraghi et al., "Long Term Results of Single Session Percutaneous Ethanol Injection in Patients with Large Hepatocellular Carcinoma", Cancer, vol. 83(1), 1998, pp. 48-57.

Bernard H. Bochner et al., "The Promise of Antiangiogenic Therapies", Contemporary Urology, Jun. 2001, pp. 51-57.

M. Wirth et al, "Bicalutamide (CASODEX) 150 mg As Immediate Therapy in Patients with Localized or Locally Advanced Prostate Cancer Significantly Reduces the Risk of Disease Progression", Elsevier Science Inc., Urology 58 (2) 2001, pp. 146-151.

Lars Magne Eri et al, "Can Prostate Epithelial Content Predict Response to Hormonal Treatment of Patients wit Benign Prostatic Hyperplasia?", Elsevier Science Inc., Urology 56 23) 2000, pp. 261-266.

Lars Magne Eri et al, "The Effect of Bicalutamide on Prostate Histology", The Prostate, vol. 46, 2001, pp. 275-280.

American Medical Systems, Inc., Poster presented at the 94th Annual Meeting American Urological Association, Dallas, Texas, May 1-6, 1999, "Transurethral Ethanol Ablation of the Prostate", presented by Joseph V. DiTrolio.

American Medical Systems, Inc., Poster presented at the 2001 AUA NewYork Sectional Meeting, Sep. 2001, "Transurethral ethanol Ablation of the Prostate (TEAP) for BPH—A Promising New Minimally-Invasive Treatment", presented by Joseph V. DiTrolio.

Author unknown, "Prostate Pathology", 6 pages, downloaded Jun. 3, 2002, http://medlib.med.utah.edu/WebPath/Tutorial/Prostate/Prostate.html.

Greg Melsen, "American Medical System Launches Phase I/II Clinical Trials of AMS ProstaJect ™ Ethanol Injection System" 1 page, downloaded Mar. 29, 2002, http://headlines.urologynet.org/inf/$headline.exe/Urology/ViewMessge?9436.

Notification of Transmittal of the International Search Report or the Declaration, mailed Sep. 17, 2003 (4 pages).

* cited by examiner

REGIMEN FOR TREATING PROSTATE TISSUE AND SURGICAL KIT FOR USE IN THE REGIMEN

REFERENCE TO RELATED APPLICATION

This application claims the benefit of U.S. Provisional Application No. 60/304,149 filed Jul. 10, 2001 and entitled "Method of Treating Prostate Tissue and Surgical Kit for Use in the Method," the entire disclosure of which is hereby incorporated by reference. This application also claims the benefit of U.S. Provisional Application No. 60/329,262 filed Oct. 12, 2001 and entitled "Surgical Instrument and Method," the entire disclosure of which is hereby incorporated by reference.

TECHNICAL FIELD

The present invention relates to treatment regimens for treating diseased prostate tissue, and to surgical kits for use in a treatment regimen.

Prostate disease is a significant health risk for males. Diseases of the prostate include prostatitis, benign prostatic hyperplasia (BPH, also known as benign prostatic hypertrophy), and prostatic carcinoma.

Prostatitis is an inflammation of the prostate gland. Symptoms of prostatitis can include difficult urination, burning or painful urination, perineal or lower back pain, joint or muscle pain, tender or swollen prostate, blood in the urine, or painful ejaculation. Prostatitis is caused by bacterial infection in many instances, in which case treatment generally includes antimicrobial medication. Noninfectious forms of prostatitis are treated by other means, such as administration of an $\alpha_1$-adrenoreceptor antagonist drug to relax the muscle tissue in the prostate and reduce the difficulty in urination.

Benign prostatic hypertrophy is a very common disorder, affecting an estimated 12 million men in the United States alone. BPH is a chronic condition and is strongly age-related; approximately 50% of men over the age of fifty, 75% of men beyond the age of seventy, and 90% of men over the age of eighty are afflicted with BPH. BPH is a non-cancerous condition characterized by enlargement of the prostate, obstruction of the urethra and gradual loss of bladder function. Symptoms include difficult urination, frequent urination, incomplete emptying of the bladder, and urgency.

BPH is treated with a number of therapeutic modalities, including surgical and medical methods. Transurethral resection of the prostate (TURP) is a preferred surgical method of treating BPH. A typical TURP procedure requires general anesthesia, and the placement of a resectoscope in the urethra for removal of multiple small chips of hyperplastic prostatic tissue, to relieve the obstruction. Complications from TURP include bleeding, incontinence, retrograde ejaculation and impotence.

An alternative surgical method for treating BPH is transurethral incision of the prostate (TUIP). In the TUIP procedure, incisions are made in the prostate to relieve pressure and improve flow rate. Incisions are made where the prostate meets the bladder. No tissue is removed in the TUIP procedure. Cutting muscle in this area relaxes the opening to the bladder, which decreases resistance to urine flow from the bladder. A variant of the TUIP procedure in which a laser is used to make the incision is known as transurethral laser incision of the prostate (TULIP).

Other surgical methods used to relieve the symptoms of BPH include methods of promoting necrosis of tissue that blocks the urethra. Hyperthermic methods, for example, use the application of heat to "cook" tissue and kill the cells. The necrosed tissue is gradually absorbed by the body. Several methods of applying heat or causing necrosis have been utilized, including direct heat (transurethral needle ablation, or TUNA), microwave (transurethral microwave treatment, or TUMT), ultrasound (high-intensity focused ultrasound, or HIFU), electrical vaporization (transurethral electrical vaporization of the prostate, or TUEVP) and laser ablation (visual laser ablation of the prostate, or VLAP), among others.

Chemical ablation (chemoablation) techniques for promoting prostate tissue necrosis are also currently under development. In one chemical ablation technique, absolute ethanol is injected transurethrally into the prostate tissue. This technique is known as transurethral ethanol ablation of the prostate (TEAP). The injected ethanol causes cells of the prostate to burst, killing the cells. The prostate shrinks as the necrosed cells are absorbed. Generally no tissue sloughing is observed with this technique. As a treatment for BPH transurethral injection of ethanol is cost-effective and is reported to have few complications; see Goya, et al., *J. Urol.* 162, 383 (1999). Transperineal ethanol injection has been reported to be effective in the treatment of BPH; see Savoca, et al., *Eur. Urol.* 40, 504 (2001). Ethanol ablation methods have also been investigated for treatment of prostatic carcinoma (Amano, et al., *Urology* 59, 771 (2002)) and liver cancer (Livraghi, et al., *Cancer* 83, 48 (1998)).

Several drugs have been approved in the United States for the treatment of BPH. One class of drugs used in treating BPH is the inhibitors of the enzyme 5α-reductase. 5α-reductase plays a role in the conversion of testosterone to the potent androgenic hormone 5α-dihydrotestosterone DHT). The role of androgens in the development of benign prostatic hyperplasia in men is well-documented; see Wilson, *N. Engl. J. Med.* 317, 628 (1987). The enlargement of the prostate gland is dependent on DHT. DHT is bound to cytosol androgen receptors within the cytoplasm, and the DHT-receptor complex is subsequently transported into the cell nucleus, where it leads to translation and transcription of genetic material.

The enzyme 5α-reductase exists in the forms Type I and Type II. Type II is predominantly expressed in the prostate. Treatment by an inhibitor of 5α-reductase can reduce the production of DHT and slow the growth of prostatic tissue.

Finasteride (PROSCAR), a synthetic 4-azasteroid compound, acts by inhibiting the Type-II form of 5α-reductase. Finasteride has the chemical name (5α,17β)-N-(1,1-dimethylethy)-3-oxo-4-azaandrost-1-ene-17-carboxamide. Finasteride inhibits 5α-reductase by forming a stable complex with the enzyme. Finasteride is reported to have no affinity for the androgen receptors in the cytoplasm. Treatment with finasteride reduces production of DHT.

U.S. Pat. Nos. 4,220,735, 4,377,584, and 4,760,071 to Rasmusson, et al. describe the synthesis of finasteride and related compounds. The use of finasteride can actually shrink the prostate in some men. It is thought that the herbal supplement saw palmetto, commonly taken for prostate health, also acts to inhibit 5α-reductase and reduce DHT levels to some degree.

Dutasteride (DUAGEN), (5α,17β)-N-[2,5-bis(trifluoromethy)phenyl]-2-oxo-4-azaandrost-1-ene-17-carboximide, is a recently approved synthetic 4-azasteroid drug that is reported to inhibit both Type I and Type II 5α-reductase. Another so-called "dual inhibitor" is designated PNU 157706, [N-(1,1,1,3,3,3-hexafluorophenyl-propyl)-3-oxo-4-aza-5α-androst-1-ene-17β-carboxamide]; see diSalle, et al., *J Steroid Biochem. Mol. Biol.* 64, 179 (1998).

Also approved for treatment of BPH are the $\alpha_1$-adrenoreceptor antagonist (or α-blocker) drugs, including terazosin (HYTRIN, doxazosin (CARDURA) and tamsulosin FLOMAX). These $\alpha_1$-adrenoreceptor antagonist drugs act to relax the smooth muscle of the prostate and bladder neck, resulting in improved urine flow and reduced bladder outlet obstruction. However, administration of an $\alpha_1$-adrenoreceptor antagonist treats only the symptoms of BPH, and does not treat the enlarged prostate itself.

U.S. Pat. No. 5,753,641 to Gormley, et al. reports a method of treating BPH using a combination of a 5α-reductase inhibitor, such as finasteride, and an $\alpha_1$-adrenoreceptor antagonist, such as terazosin. A method of treating BPH with a combination of an $\alpha_1$-adrenoreceptor antagonist, such as terazosin, and saw palmetto extract is reported in U.S. Pat. No. 6,200,573 to Locke. Treatment of BPH by the administration of the non-steroidal antiandrogen bicalutamide is reported by Eri, et al., *Urology* 56, 261 (2000).

Prostate cancer (prostatic carcinoma), is a common cancer among males and a leading cause of cancer deaths in males beyond the age of fifty. Prostate cancer begins as a tumor on the prostate gland. Prostate cancer confined to the gland often can be treated successfully. If untreated, the cancer may spread to tissues near the prostate, to seminal vesicles, and to distant parts of the body, such as bones, liver, or lungs. Often, the cancer is slow-growing, which permits the course of treatment known as "watchful waiting" for elderly patients or patients in poor health. More aggressive treatments are required if the disease progresses. Radiation treatments, surgical procedures, and medical treatment are all possible courses of action.

Radiation therapy may be appropriate at certain stages of prostate cancer. Brachytherapy is appropriate at early stages of the disease, and can be highly effective. Brachytherapy involves implantation of radioactive particles into the tumor. The particles emit radiation over a period of a few months, which kills the cancerous tissue. External radiation treatment (XRT) is prescribed when the cancer has spread to surrounding tissue. High-energy x-rays are directed to the prostate region from outside the body. Treatment is continued for about eight weeks on an outpatient basis.

Surgical intervention for prostate cancer typically involves a radical prostatectomy via an abdominal (retropubic) or perineal approach. Radical prostatectomy is a surgical procedure involving the substantially complete removal of prostate tissue. Advanced techniques such as nerve sparing radical prostatectomy or nerve grafting seek to improve outcomes and reduce complications. Impotence and incontinence are side-effects commonly associated with surgical removal of the prostate.

Cryosurgery, or cryoablation, is also commonly used to kill cancerous tissue at the prostate. In cryoablation, tissue is rapidly and repeatedly frozen and thawed to kill the tumor. The procedure is generally done on an outpatient basis and takes only a few hours. One method of reducing prostate tissue volume using a combination of cryotherapy and hyperthermia is reported in U.S. Pat. No. 6,378,525 to Beyar, et al.

It is known that androgen deprivation can slow the progression of cancer originating in the prostate. Androgen deprivation may be achieved by either surgical or chemical castration. The organ that is the primary source of male androgenic hormones in the body is the testicles. Surgical removal of the testicles is known as an orchiectomy. The majority of patients who undergo an orchiectomy will experience diminished libido and erectile dysfunction. Other undesirable side effects are also common, including weight gain, depression, fatigue, mood swings, and hot flashes.

Androgen deprivation is usually achieved by chemical castration through hormone therapy, in which testosterone is generally the androgen targeted for depression. Hormone therapy deprives cancerous cells of testosterone, a hormone which is necessary for cell growth. Luteinizing hormone-releasing hormone (LHRH) normally stimulates the pituitary gland to release luteinizing hormone, which in turn stimulates the testes to produce testosterone. In the prostate cells, testosterone is converted to DHT by the enzyme Type II 5α-reductase. DHT then binds to cytoplasmic androgen receptors, and the DHT-receptor complex enters the cell nucleus where it activates transcription of androgen-dependent genes.

Luteinizing hormone-releasing hormone analogues (also known as gonadotropin-releasing hormone agonist analogues, or GnRH analogues) are used to block the production of testosterone by the testes. Leuprolide acetate (LUPRON DEPOT, PROSTAP), goserelin acetate (ZOLADEX), buserelin acetate (available outside the U.S. as SUPREFACT), and triptorelin pamoate (TRELSTAR LA) are LHRH analogues shown to reduce serum testosterone levels. Administration of an LHRH analogue is often accompanied by an initial surge in testosterone and DHT levels for about 5 to 12 days before inhibition of leutenizing hormone, however.

Administration of an antiandrogen drug may be prescribed in combination with an LHRH analogue in the treatment of prostate cancer. Antiandrogens are a class of drugs that specifically block the entry of androgenic hormones into cells of the body, thus preventing its biological effects. It is thought that antiandrogens competitively inhibit the action of androgenic hormones, such as DHT, by binding to cytosol androgen receptors, and preventing DHT from binding to the receptors and entering the cell nucleus. Antiandrogen drugs that are used in hormone therapy include steroidal drugs and non-steroidal drugs.

Steroidal antiandrogen drugs used in hormone therapy include progestin compounds such as cyproterone acetate (available outside the U.S. as ANDROCUR or CYPROSTAT), megestrol acetate (MEGACE), medroxyprogesterone acetate (PROVERA), and chlormadinone acetate (available in Japan). Zanoterone (designated WIN 49596) is also a steroidal antiandrogen drug that may be useful in hormonal therapy.

Non-steroidal antiandrogen drugs used in hormone therapy include bicalutamide (CASODEX), nilutanide (NILANDRON; ANANDRON, and flutamide (EULEXIN; DROGENIL outside the U.S.). A new non-steroidal antiandrogen compound, designated RU 58642, is currently being developed and reportedly is more potent in reducing prostate weight than antiandrogens presently used; see Battman, et al., *J. Steroid Biochem. Mol. Biol.* 64, 103 (1998). The non-steroidal antiandrogen RU 58841 has been explored as a topical treatment for hair loss, but may also be effective in hormone therapy for prostate diseases.

The use of non-steroidal antiandrogens alone (i.e., not in combination with an LHRH analogue) has not been shown to be effective in the treatment of progressing prostate cancer. Recent reports, however, indicate that bicalutamide may be effective to reduce the risk of disease progression in patients with localized or locally advanced prostate cancer, see Wirth, et al., *Urology* 58, 146 (2001). In clinical trials with bicalutamide as a single agent for prostate cancer, rises in serum testosterone and estradiol have been observed.

A combination of a 5α-reductase inhibitor, such as finasteride, and a non-steroidal antiandrogen, such as flutamide or bicalutamide, is reported in U.S. Pat. No. 5,994,362 to Gormley, et al. as a candidate for effective treatment of prostatic cancer, see also Fleshner, et al., *J. Urol.* 154, 1642 (1995).

Luteinizing hormone-releasing hormone receptor antagonists (also known as gonadotropin-releasing hormone receptor antagonists, or GnRH receptor antagonists) have recently been studied for the treatment of prostatic cancer, see Cook, et al., *Oncologist* 5, 162 (2000); Stricker, *Urology* 58 (Supp. 2A), 24 (2001); Trachtenberg, et al., *J. Urol.* 167, 1670 (2002). LHRH antagonists are expected to inhibit leutenizing hormone without an initial surge in testosterone and DHT levels. LHRH antagonists that have shown promise for prostate treatment include cetrorelix acetate (CETROTIDE) and abarelix (PLENAXIS). U.S. Pat. No. 6,022,860 to Engel, et al. reports a activity-stabilized and release-delayed complex including an LHRH antagonist such as antide, antarelix, azaline, A-75998, ganirelix, Nal-Glu antagonist, or cetrorelix.

Many hormonal therapies are accompanied by highly undesirable side effects, including impotence, loss of sexual desire, hot flashes, and gynecomastia (i.e., swelling or tenderness of breasts), among others. Diarrhea is also a common side effect for patients taking flutamide.

SUMMARY OF THE INVENTION

In one embodiment, the present invention provides a treatment regimen for treating diseased prostate tissue. The treatment regimen includes the steps of chemically ablating prostate tissue sufficiently to elicit a reparative process in the absence of further treatment; and coadministering a therapeutically effective amount of an antiandrogen. The size of the prostate is reduced relative to its size prior to treatment by the treatment regimen. The treatment regimen is suitable for treatment of prostate tissue diseases including BPH and prostatic carcinoma.

In another embodiment, the present invention provides a treatment regimen for treating benign prostatic hyperplasia The treatment regimen includes the steps of necrosing hyperplastic prostate tissue sufficiently to elicit a reparative process in the absence of further treatment; and coadministering a therapeutically effective amount of an antiandrogen. The size of the prostate is reduced relative to its size prior to treatment by the treatment regimen.

In yet another embodiment, the present invention provides a treatment regimen for treating benign prostatic hyperplasia. The treatment regimen includes the steps of damaging hyperplastic prostate tissue sufficiently to elicit a reparative process in the absence of further treatment; and coadministering a therapeutically effective amount of an antiandrogen. The size of the prostate is reduced relative to its size prior to treatment by the treatment regimen.

Another embodiment of the present invention also provides a treatment regimen for treating prostate diseases. The treatment regimen of this embodiment includes the steps of injecting an effective amount of ethanol into prostate tissue to ablate a significant amount of prostate tissue; and coadministering a therapeutically effective amount of an antiandrogen. The size of the prostate is reduced relative to its size prior to treatment by the treatment regimen. The treatment regimen is suitable for treatment of prostate tissue diseases including BPH and prostatic carcinoma.

Also provided by the present invention is a treatment regimen for treating benign prostatic hyperplasia, including the steps of necrosing hyperplastic prostate tissue by injecting an effective amount of ethanol into a prostate; and coadministering a therapeutically effective amount of an antiandrogen. The size of the prostate is reduced relative to its size prior to treatment by the treatment regimen.

The present invention further provides a kit for treating a human male. The kit of this embodiment includes a means for necrosing prostate tissue, a therapeutically effective amount of an antiandrogen drug, and a means for administering the antiandrogen drug.

Another embodiment of the present invention provides a kit for treating a human male. The kit of this embodiment includes a first surgical device having a needle for delivering a chemoablation fluid to prostate tissue transurethrally, a therapeutically effective amount of an antiandrogen drug such as bicalutamide, and a second surgical device for administering the antiandrogen drug.

DETAILED DESCRIPTION OF THE INVENTION

In one embodiment, the present invention provides a treatment regimen for treating diseased prostate tissue. The treatment regimen includes the steps of chemically ablating prostate tissue sufficiently to elicit a reparative process in the absence of further treatment; and coadministering a therapeutically effective amount of an antiandrogen. The size of the prostate is reduced relative to its size prior to treatment by the treatment regimen. The treatment regimen is suitable for treatment of prostate tissue diseases including BPH and prostatic carcinoma.

Figure 1:
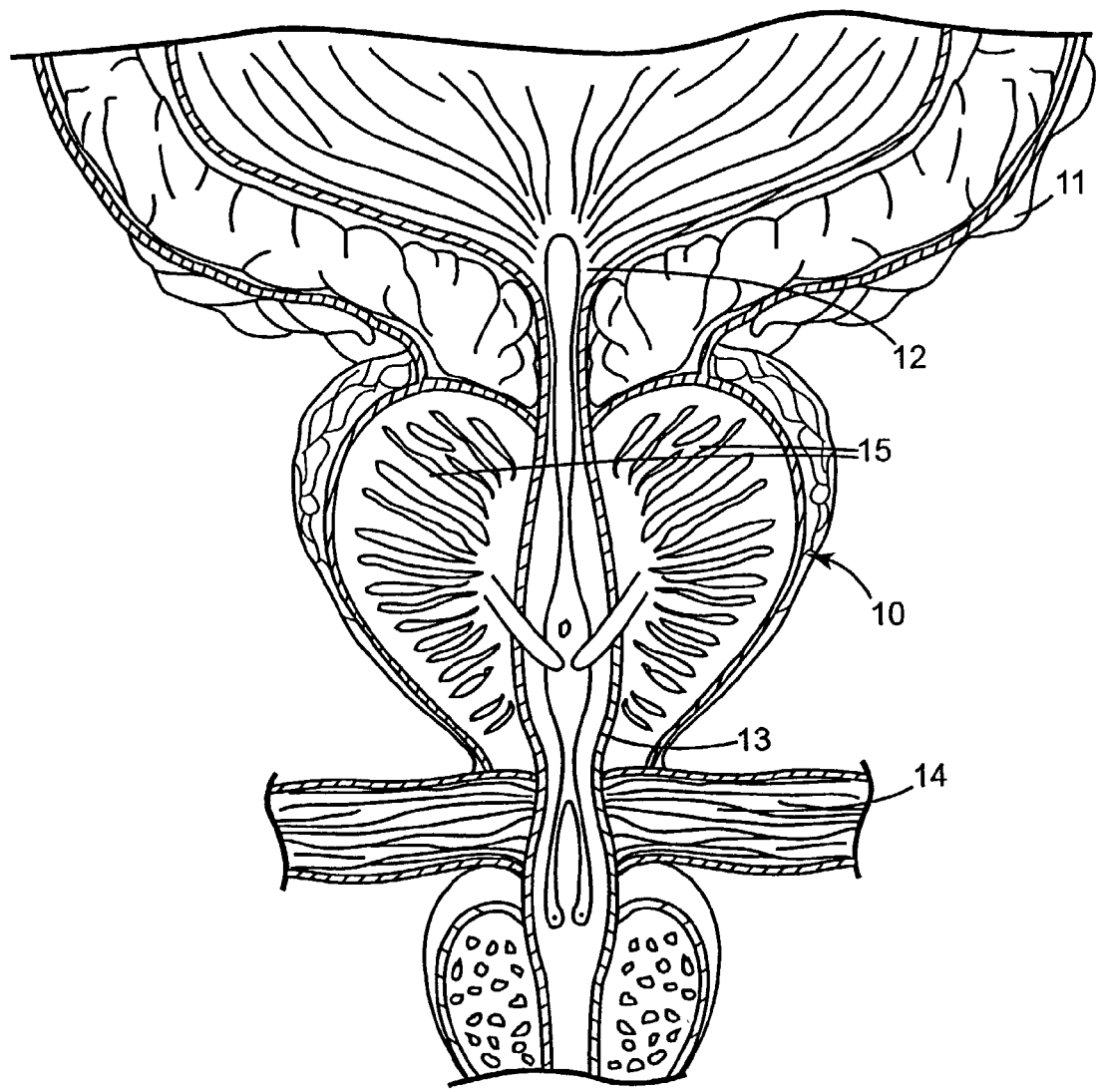
FIG. 1 is an anatomical drawing showing the location of the prostate.

FIG. 1 shows the anatomical position of prostate 10 (including lateral lobes 15) surrounding urethra 13, and adjacent tissue including seminal vesicles 11, bladder neck 12, and pelvic tissues including sphincter muscles 14. Chemical ablation may be achieved, for example, by direct injection of a chemoablation fluid into a patient's prostate. As used throughout this specification, the terms "ablate," "ablation" or "ablating" of tissue means causing a reduction in tissue mass. One suitable manner of ablating tissue is by causing a decrease in the number of tissue cells. The phrase "chemical ablation" includes processes whereby tissue mass is reduced by action of a chemical or biological agent on the tissue.

One suitable procedure for chemically ablating prostate tissue in accordance with the treatment regimen is by injection of ethanol (absolute alcohol) into the prostate to be treated. Ethanol preferably is injected deeply into prostate tissue through a needle that is positioned transurethrally, such as in the procedure known as transurethral ethanol ablation of the prostate (TEAP). The ablating action of ethanol is due to several processes, including dehydration of cells, coagulation of proteins, and thrombosis of vessels that feed the tissue.

Prior to the TEAP procedure, measurements of the patient's prostate should be made. Dimensions of interest include the maximum transverse diameter, length (i.e., prostatic urethral length), and height (i.e., transverse diameter perpendicular to the maximum transverse diameter), and transverse diameter at the verumontanum. One method known to practitioners for determining the dimensions of interest is transrectal ultrasound, or TRUS.

Figure 2:
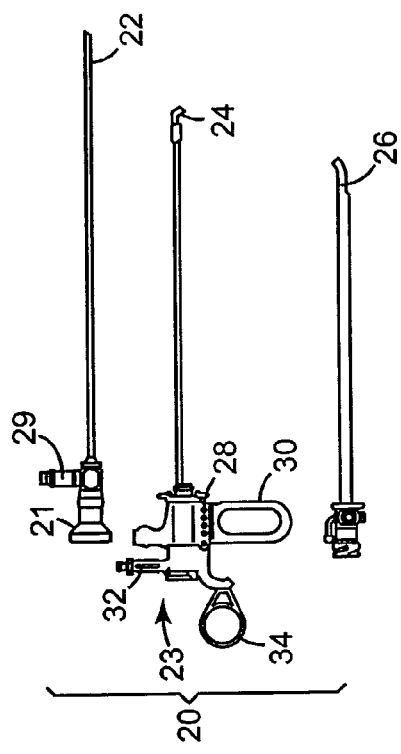
FIG. 2 is a side view of a disassembled surgical device for use in various embodiments of the present invention.
Figure 3:
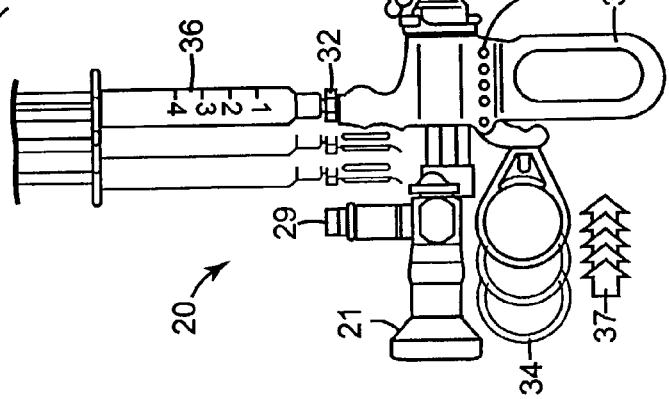
FIG. 3 is a side view of the surgical device of FIG. 2 in an assembled condition.

After measurements of the patient's prostate have been obtained, the TEAP procedure may be performed. FIGS. 2 and 3 show a surgical device 20 suitable for use in chemically ablating prostate tissue by ethanol injection. A device as shown in FIG. 2 is commercially available under the trade name PROSTAJECT from American Medical Systems, Inc. of Minnetonka, Minn.

A PROSTAJECT device with improved needle visualization and control features is a preferred surgical device for use in accordance with the present invention. Improvements to surgical devices such as the PROSTAJECT device are disclosed in U.S. Provisional Patent Application No. 60/329,262, filed Oct. 12, 2001, entitled, "Surgical Instrument and Method," the entire contents of which is herein incorporated by reference. Alternatively, simple hypodermic or transperineal needles (e.g., for use in brachytherapy procedures) may also be used in accordance with the present invention.

FIG. 2 shows the device 20 in an unassembled condition and FIG. 3 shows the device 20 in an assembled condition. The device 20 includes a scope sheath 22 with eye port 21 and port 29 for a light source or for irrigation; a hollow outer sheath 26; and a main body 23 with a needle deployment port 24, syringe port 32, retractable needle 25 (not shown in FIG. 2), handle 30 and thumb ring 34. Scope 22 may be a commercially available rigid endoscope such as a cystoscope or laparoscope, for example. Suitable cystoscopes are available, for example, from ACMI (Classic and Elite models), Storz, Wolf and Olympus. The needle 25 is preferably a hollow curved needle having needle tip 27. The main body 23 includes syringe port 32 that is designed to mate with a syringe 36 having a threaded LUER LOK connector. Detents 28 are provided for precise needle advancement through auditory, visual and tactile confirmation of the positioning of needle tip 27 in a lobe of the prostate. Arrows 39 shown in FIG. 3 demonstrate the advancing motion of needle 25 and needle tip 27 of the surgical device 20 as thumb ring 34 is advanced, as shown by arrows 37.

Briefly, to perform the TEAP procedure using surgical device 20, outer sheath 26 is positioned in the patient's urethra Scope sheath 22 and main body 23 are assembled and advanced into the outer sheath 26 to position needle deployment port 24 within the patient's prostatic urethra. The scope sheath 22 via eye port 21 allows visual positioning of the needle deployment port 24 against the prostatic urethra at an injection site adjacent to a lobe of the prostate to be treated. The needle deployment port 24 should be positioned such that the injection site is at least 1.0 cm distal from the bladder neck and clearly proximal to the verumontanum. The retractable needle 25 is advanced (as shown by arrows 39 in FIG. 3) one detent-click at a time (0.5 cm per detent) to puncture the urethral wall at the injection site and to place the needle tip 27 into the lobe of the prostate. It is critical that the needle tip 27 is not advanced so far into the prostate as to violate the prostate capsule; a safety margin of at least 1.0 cm is recommended. The safe maximum extension of the needle tip 27 into the lateral lobes of the prostate may be determined by the following equation:

Maximum needle tip extension=$(0.5 \times D1) - 1.0$ cm (Equation 1);

where D1 is the transverse diameter of the prostate at the injection site (measured in cm). The transverse diameter is measured preoperatively by, for example, TRUS.

A syringe 36 containing approximately 5 mL of ethanol is mated with syringe port 32. A small volume (e.g. 3 to 5 mL per injection site) of ethanol is slowly injected from the syringe 36 through the needle 25 into the prostate tissue at the injection site, using low pressure. The urethral lumen may be continuously irrigated via port 29 while the ethanol is being administered, to prevent ethanol from coming into prolonged contact with tissues other than the prostate. The needle 25 should be left in place for approximately one minute after the injection is complete, to permit the injected ethanol to diffuse into the prostate tissue. The needle tip 27 is then withdrawn and the assembly of scope sheath 22 and main body 23 is removed from the outer sheath 26. The patient's bladder may then be emptied, and the device 20 may be rotated to target another transurethral access point.

An injection of ethanol is similarly made into each lateral lobe of the prostate to complete a first plane of injections. Blanching of prostate tissue can be observed nearly immediately, indicating that tissue ablation is occurring. In cases with median lobe enlargement (i.e., where hyperplasia is present in the median lobe), an ethanol injection may be made to the median lobe of the prostate. Generally only about 2–3 mL of ethanol should be injected into the median lobe. The needle tip 27 should be extended no more than 1.0 cm into the median lobe.

In cases of longer prostatic urethra, such as where prostatic urethral length is measured as greater than 2 cm, a second plane of ethanol injections may be administered. (Prostatic urethral length may be measured preoperatively by using a measuring catheter and known techniques.) The second plane of injections, where necessary, should be separated from the first plane by approximately 0.5 cm, and should be at least 1.0 cm distal from the bladder neck.

The TEAP procedure may typically be performed by a skilled practitioner in about twenty minutes. The patient may be catheterized using a Foley catheter following the series of ethanol injections and after removal of the outer sheath 26 from the urethra. The catheter may generally be removed after 48–72 hours. Prophylactic antibiotic therapy may be employed after treatment to diminish the risk of urinary tract infection.

The total amount of ethanol injected will depend on a variety of factors including, but not limited to the size of the prostate to be treated, the shape of the prostate (i.e., length and width), the number of injection sites determined, whether the median lobe is enlarged, and the nature and degree of prostate disease. The recommended total dosage of ethanol is about 20% to 28% of the measured volume of the prostate to be treated, and should not generally exceed 40% of the measured volume. A number of methodologies can be employed to estimate prostate volume, including magnetic resonance imaging (MRI), transrectal ultrasonography TRUS), digital rectal examination (DRE), and serum prostate specific antigen (PSA) level. By way of example, prostatic volume may be estimated using measurements of interest obtained from TRUS by the ellipsoid formula:

Volume$\approx (0.5233) \times D \times H \times L$ (Equation 2);

where D is the maximum transverse diameter of the prostate (measured in cm), H is height (measured in cm), and L is length (measured in cm).

The total amount of ethanol injected into a patient's prostate during the TEAP procedure could range from about 8 mL to about 20 mL or more; generally, no more than 26 mL would be injected under normal circumstances. However, the amount of ethanol delivered varies according to surgeon preferences, and may be greater than 26 mL in cases where the patient's prostate is severely enlarged. A total of about 13 mL is normally the average amount of ethanol injected per patient. In cases of longer prostatic urethra, such as where prostatic urethral length is measured as greater than 2 cm, a second plane of ethanol injections may be administered. Consequently, the average amount of ethanol injected would be about 26 mL for patients with prostatic urethral length greater than 2 cm. The total dosage of ethanol should generally be distributed to provide equal amounts to lateral lobes, with a somewhat smaller amount injected into the median lobe, as required.

The total number of ethanol injection sites is preferably four or fewer under normal circumstances, but the number of injection sites varies according to surgeon preferences, and may be greater than four in some cases.

By way of example, for a patient having a measured prostate volume of about 40 cc, a prostatic urethral length of less than 2.0 cm, and not exhibiting median lobe enlargement, the following injection schedule would be recommended: 5 mL injected into right lateral lobe; 5 mL injected into left lateral lobe. For a patient having a measured prostate volume of about 40 cc, a prostatic urethral length of greater than 2.0 cm, and not exhibiting median lobe enlargement, the following injection schedule would be recommended: 4 mL injected into right lateral lobe in a first plane; 4 mL injected into left lateral lobe in the first plane; 4 mL injected into right lateral lobe in a second plane; 4 mL injected into left lateral lobe in the second plane.

For a patient having a measured prostate volume of about 40 cc, a prostatic urethral length of greater than 2.0 cm, and exhibiting median lobe enlargement, the following injection schedule would be recommended: 5 mL injected into right lateral lobe; 5 mL injected into left lateral lobe; 3 mL injected into median lobe. For a patient having a measured prostate volume of about 40 cc, a prostatic urethral length of greater than 2.0 cm, and exhibiting median lobe enlargement, the following injection schedule would be recommended: 3 mL injected into right lateral lobe in a first plane; 3 mL injected into left lateral lobe in the first plane; 2 mL injected into median lobe in the first plane; 3 mL injected into right lateral lobe in a second plane; 3 mL injected into left lateral lobe in the second plane; 2 mL injected into median lobe in the second plane.

Where ethanol is used to chemically ablate prostate tissue, medical-grade ethanol (also known as anhydrous alcohol, absolute alcohol, or absolute ethyl alcohol should be employed in the treatment regimens and for the kits of the present invention. For example, 190–200 proof ethanol that meets guidelines established by the United States Pharmacopeia/National Formulary (USP/NF) is a suitable chemoablation fluid in the treatment regimens of the present invention.

Optionally, a chemoablation fluid to be injected may be combined with an additive that enhances delivery or distribution of the chemoablation fluid within the prostate tissue, or that enhances the efficacy of the chemoablation fluid. The additive may be incorporated to disperse the chemoablation fluid in the vasculature of the prostate tissue more effectively, or it may be incorporated to retain the chemoablation fluid within the prostate tissue and avoid extravasation beyond prostate tissue (i.e., beyond the prostatic capsule).

In some embodiments of the invention, an additive is added to the chemoablation fluid to form an injectable gel. By way of example, a suitable additive for forming an injectable gel is a medical-grade gelling agent. One such gelling agent is GELFOAM Sterile Powder (Pharmacia & Upjohn, Kalamazoo, Mich.). GELFOAM is a gelatin powder consisting of particles in the 40–60 micron size range and is commonly used as an embolizing agent. In particular, ethanol may be combined with an additive such as GELFOAM to form an injectable gel. In another embodiment, an additive such as a gelling agent may be injected sequentially, either before or after injection of ethanol.

An additive for enhancing visibility of the chemoablation fluid may be incorporated. For example, the additive may comprise a dye for enhancing visualization of the chemoablation fluid during injection. Better visualization of the chemoablation fluid may assist some surgeons to more effectively deliver the chemoablation fluid to the prostate tissue and to avoid undesirable backflow. By way of example, representative dyes include methylene blue, indigo carmine, india ink, malachite green, indocyanine green, and toluidine blue. In particular, methylene blue is suitable for use with ethanol.

An alternative procedure for chemically ablating prostate tissue by transurethral injection is described in Goya, et al., *J. Urol.* 162, 383 (1999). Other methods of chemically ablating prostate tissue are also suitable for the practice of the present invention. By way of example, transperineal or percutaneous injection of ethanol into prostate tissue is effective for chemically ablating prostate tissue; see Savoca, et al., *Eur. Urol.* 40, 504(2001), which is hereby incorporated by reference. Transrectal injection of ethanol and laparoscopic injection of ethanol are also suitable methods for chemically ablating prostate tissue. Transurethral, transperineal, percutaneous, transrectal or laparoscopic injection of alternative chemical ablation agents may also be employed.

Suitable alternative chemical ablation agents include toxins whose effect can be substantially contained to the tissue to be ablated. By way of example, other alcohols, certain enzymatic solutions, and some antibiotics may be suitable agents for chemically ablating prostate tissue. In addition, other dehydrating solutions such as concentrated saline solution may also be suitable chemoablation agents.

As an example of a suitable alcohol, phenol (carbolic acid) has been injected prostatically to ablate prostate tissue as a treatment for BPH. A sterile aqueous mixture of phenol, glacial acetic acid, and glycerine has been employed; see Choudhury, et al., *Brit J Urol* 52, 204 (1980) and Talwar, et al., *Brit J Surg* 53, 421 (1966), each of which is incorporated herein by reference.

The use of transurethral intraprostatic injection of an enzymatic solution to chemically ablate prostate tissue is described in U.S. Pat. No. 5,116,615 to Gokcen, et al., which is incorporated herein by reference. An effective solution reported by Gokcen, et al. includes the enzymes collagenase and hyaluronidase, a nonionic surfactant, and an antibiotic. Enzymes reported to be effective for chemically ablating prostate tissue include: collagenase, hyaluronidase, elastase, trypsin, chymotrypsin, pronase, DNase I, bromelain, clostripain, thermolysin, neuraminidase, phospholipase, cholesterol esterase, dispase, subtilisin, papain, chymopapain, plasminogen activator, plasmin, streptokinase, urokinase, fibrinolysin, serrathiopeptidase, pancreatin, amylase, lysozyme, cathepsin-G, and the PMN (polymorphonuclear) leukocyte serine proteases. These enzymes, set forth as examples only, may be suitable for chemically ablating prostate tissue in the treatment regimens of the present invention.

Direct prostatic injection of antibiotics has been researched as a treatment for prostatitis. Injection of penicillin is reported to be an effective treatment for prostatitis, and streptomycin was also tried; see Hatch, *J Urol* 64, 763 (1950). Injection of amikacin, cefazolin, gentamicin, and thiamphenicol glycinate is reported by Baert, et al., *Urology* 21, 370 (1983). Under appropriate conditions, these or other antibiotics may be suitable as chemoablation agents in the treatment regimens of the present invention.

The step of chemically ablating prostate tissue should be carried out sufficiently to elicit a reparative process in the absence of further treatment. As used herein, the phrase "reparative process" includes natural responses of the body to heal or regrow tissue in response to disease, damage, necrosis or ablation, and includes processes such as vasoconstriction, vasodilation, inflammation, phagocytosis, scarring, angiogenesis, cell growth and cell division.

The treatment regimens of the present invention include the coadministration of an antiandrogen in conjunction with ablation or necrosis of prostate tissue. Once prostate tissue is ablated or necrosed, the antiandrogen treatment is thought to adversely affect prostate tissue cell recovery and subsequent growth of any residual prostate tissue. As a result of the coadministration of an antiandrogen, the size of the prostate is reduced relative to its size prior to treatment. The size reduction is either a reduction in prostate mass or prostate volume, or both.

The step of coadministering a therapeutically effective amount of an antiandrogen may occur prior to, during, or after the step of ablating or necrosing the prostate tissue. The timing of the coadministering step will depend upon a variety of factors including physician choice and treatment strategy. As used herein, the term "coadministering" indicates that the antiandrogen is administered as part of a planned course of treatment for a prostate condition, in conjunction with a procedure for ablating or necrosing prostate tissue.

The phrase "therapeutically effective amount" means an amount of antiandrogen that, when coadministered according to the treatment regimens of the invention, provides the desired inhibition of growth or reduction in size of the prostate for the patient. Indicators of successful therapy include the reduction in size of the obstructive prostatic tissue and, in the case of treatment for BPH, the subsequent alleviation of symptoms of urinary obstruction. Objective assessment of the effects of therapy may measured by standard methods, including urodynamic flow analysis, transurethral examination, or transrectal ultrasonography, or by an obstructive symptom scoring questionnaire such as the International Prostate Symptom Score (IPSS) or the American Urological Association Symptom Index Score (AUA Score).

In determining a proper dosage for the antiandrogen in the treatment regimens of the invention, certain guidelines should be observed. Administration of any antiandrogen in the treatment regimens of the present invention should not exceed maximum dosage levels established by the United States Food and Drug Administration or published in the *Physician's Desk Reference*. It is desirable to dose the minimum therapeutically effective amount that will achieve the desired inhibition of growth or reduction in size of the prostate for the patient, in order to diminish unwanted side effects resulting from administration of the antiandrogen.

In general, the timing of the coadministration of the antiandrogen depends upon several factors, including the type of prostate disease, the severity or advancement of the disease to be treated, whether treatment is ongoing at the time of administration, patient preferences, the type of antiandrogen to be administered, and the therapeutic intervention strategy devised by the physician. For example, some non-steroidal antiandrogens may tend to acquire agonistic properties during long-term androgen deprivation. Also, androgen-dependent diseases may mutate further and become androgen-independent. As a result, the physician and patient may decide to defer administration of antiandrogen until immediately after the prostate tissue is ablated.

Within the scope of the invention it is envisioned that the antiandrogen be coadministered up to several weeks prior to the ablating or necrosing procedure, or that the antiandrogen be coadministered weeks or even months after the ablating or necrosing procedure. Generally, the antiandrogen is coadministered either during or shortly after the procedure; however, this is not required, and the antiandrogen may be coadministered at other times.

In an embodiment of the invention, a portion of antiandrogen is administered before, and another portion is administered after the step of ablating or necrosing the prostate tissue. In another embodiment, a portion of antiandrogen is administered during the step of ablating or necrosing the prostate tissue, and another portion is administered either before or after the step of ablating or necrosing the prostate tissue.

Preferably, at least a portion of antiandrogen is administered after the step of ablating or necrosing the prostate tissue. However, treating the prostate tissue with an antiandrogen prior to ablating or necrosing the tissue may have benefits. For example, such pretreatment may desirably render the prostate tissue more susceptible to damage from an ablating or necrosing procedure, or less likely to recover from damage done during an ablating or necrosing procedure.

The antiandrogen may be administered via a variety of techniques including, but not limited to, orally in a tablet or solution, transdermally, percutaneously by injection into subcutaneous or intramuscular sites, perineally by injection into the prostate tissue, or by transurethral injection into prostate tissue. Preferably, the antiandrogen is administered orally in tablet form.

The antiandrogen may comprise a steroidal antiandrogen or a non-steroidal antiandrogen. One suitable non-steroidal antiandrogen is bicalutamide, which is available commercially under the trade name CASODEX (AstraZeneca, Wilmington, Del.). The chemical name for bicalutamide is (+−)N-[4-cyano-3-(trifluoromethy)phenyl]-3-[(4-fluoropheny)sulfonyl]-2-hydroxy-2-methyl propanimide (described in U.S. Pat. No. 4,636,505 to Tucker, which is incorporated herein by reference). In an embodiment of the invention, the antiandrogen comprises an R-enantiomer of bicalutamide.

Dosage guidelines for CASODEX published in the *Physician's Desk Reference* report that a typical dosage in a combination therapy (i.e., CASODEX in combination with an LHRH analogue) for prostatic carcinoma is once-daily oral administration of one 50-mg tablet. Dosages up to 200 mg per day are reported to be well-tolerated in long-term clinical trials. Administration of bicalutamide or any antiandrogen in the treatment regimens of the present invention should not exceed maximum dosage levels established by the United States Food and Drug Administration or published in the *Physician's Desk Reference*.

In an embodiment of the treatment regimens described herein, an oral dosage of about 150 mg bicalutamide is administered to the patient daily for approximately thirty days, beginning on the day in which the ablating or necrosing step is initiated. In a variation of this embodiment, administration of bicalutamide is continued for approximately an additional thirty days, during which an oral daily dosage of about 50 mg is administered.

In another embodiment of the treatment regimens described herein, an oral dosage of about 150 mg bicalutamide is administered to the patient daily, beginning one to two days prior to the day on which the ablating or necrosing step is initiated. Daily dosage of about 150 mg bicalutamide is continued until approximately thirty days following the initiation of the ablating or necrosing step. In a variation of this embodiment, administration of bicalutamide is further continued for approximately an additional thirty days, during which an oral daily dosage of about 50 mg is administered.

In yet another embodiment, an oral dosage of about 150 mg bicalutamide is administered to the patient daily, beginning ten days prior to the day on which the ablating or necrosing step is initiated. Daily dosage of about 150 mg bicalutamide is continued until approximately thirty days following the initiation of the ablating or necrosing step. In a variation of this embodiment, administration of bicalutamide is further continued for approximately an additional thirty days, during which an oral daily dosage of about 50 mg is administered.

Suitable non-steroidal antiandrogens also include flutamide and nilutamide. RU 58642 and RU 58841 may also be suitable non-steroidal antiandrogens. Other suitable non-steroidal antiandrogens for the practice of the present invention include non-steroidal antiandrogens described in U.S. Pat. No. 3,875,229 to Gold, U.S. Pat. No. 4,097,578 to Perronnet, et al., U.S. Pat. No. 4,239,776 to Glen, et al., U.S. Pat. No. 4,386,080 to Crossley, et al., U.S. Pat. No. 5,994, 362 to Gormley, et al., or U.S. Pat. No. 5,872,150 to Elbrecht, et al. (the entire contents of each of which is herein incorporated by reference).

The antiandrogen may also comprise a steroidal antiandrogen. Suitable steroidal antiandrogens include cyproterone acetate, megestrol acetate, medroxyprogesterone acetate, chlormadinone acetate, and WIN 49596.

The step of coadministering a therapeutically effective amount of an antiandrogen may also optionally comprise the step of administering an inhibitor of an intracellular enzyme in prostate tissue that converts the androgen testosterone into 5α-dihydrotestosterone (DHT). In particular, the inhibitor may inhibit Type II 5α-reductase. In another embodiment, the step of coadministering a therapeutically effective amount of an antiandrogen may optionally incorporate the step of administering a synthetic 4-azasteroid compound to inhibit 5α-reductase. The 4-azasteroid compounds finasteride, dutasteride, and PNU 157706 are suitable Type II 5α-reductase inhibitors for use in the present invention. Finasteride is available under the trade name PROSCAR (Merck & Co., Inc., Whitehouse Station, N.J.). Other suitable 4-azasteroid compounds are described in U.S. Pat. Nos. 4,220,735, 4,377,584, and 4,760,071 to Rasmusson, et al.

In the treatment regimens of the present invention, the dosage quantity for the inhibitor is determined in accordance with accepted guidelines for treatment of BPH. By way of example, the recommended daily dosage of finasteride is 5 mg, administered orally. Administration of an inhibitor in the treatment regimens of the present invention should not exceed maximum dosage levels established by the United States Food and Drug Administration or published in the *Physician's Desk Reference*.

Optionally, the treatment regimen may include other steps commensurate with the physician's treatment strategy. For example, the step of coadministering a therapeutically effective amount of an antiandrogen may further include the step of administering an LHRH analogue. Administering an LHRH analogue may particularly be desirable if a non-steriodal antiandrogen is employed as the antiandrogen. Suitable LHRH analogues include but are not limited to leuprolide acetate, goserelin acetate, buserelin acetate, and triptorelin pamoate.

In the treatment regimens of the present invention, the dosage quantity for the LHRH analogue is determined in accordance with accepted guidelines for androgen ablation therapies in the treatment of prostatic carcinoma. By way of example, the recommended dosage of goserelin acetate is 3.6 mg per 28 days of treatment, administered subcutaneously in implant form. Administration of an LHRH analogue in the treatment regimens of the present invention should not exceed maximum dosage levels established by the United States Food and Drug Administration or published in the *Physician's Desk Reference*.

The step of coadministering a therapeutically effective amount of an antiandrogen may optionally include the step of administering an LHRH antagonist. Suitable LHRH antagonists include but are not limited to cetrorelix and abarelix. Other suitable LHRH antagonists may include antide, antarelix, azaline, A-75998, ganirelix, or Nal-Glu antagonist. Administration of an LHRH antagonist in the treatment regimens of the present invention should not exceed any maximum dosage levels established by the United States Food and Drug Administration or published in the *Physician's Desk Reference*.

In another embodiment, the present invention provides a treatment regimen for treating benign prostatic hyperplasia. The treatment regimen includes the steps of necrosing hyperplastic prostate tissue sufficiently to elicit a reparative process in the absence of further treatment; and coadministering a therapeutically effective amount of an antiandrogen. The size of the prostate is reduced relative to its size prior to treatment by the treatment regimen.

The step of necrosing hyperplastic prostate tissue may be conducted by a variety of surgical and non-surgical techniques. As used herein, the term "necrose" or "necrosing" means to cause the death of tissue cells or of a portion of tissue. Suitable methods of inducing necrosis in hyperplastic prostate tissue include irradiation (e.g., with microwave energy, radiofrequency, ultrasound, nuclear radiation, x-rays, or laser ablation), application of heat (thermal ablation), freezing prostate tissue (cryoablation), chemical ablation, surgically damaging prostate tissue, or by electrical vaporization of prostate tissue, among others. Inducing apoptosis, or natural cell death, is also included within the meaning of the term "necrosing."

Examples of surgical devices capable of damaging prostate tissue to induce necrosis are disclosed in U.S. Pat. No. 4,461,283 to Doi, U.S. Pat. No. 5,672,171 to Andrus, et al. and U.S. Pat. No. 5,630,794 to Lax, et al., and PCT International Publication Nos. WO 92/10142 and WO 93/15664, the entire contents of each of which is herein incorporated by reference. Examples of devices and methods for surgically damaging prostate tissue to induce necrosis are disclosed in U.S. Pat. Nos. 5,322,503, 5,562,703, 5,861,002 and 6,231, 591, all to Desai, the entire contents of each of which is incorporated by reference.

Also, a medication that induces necrosis of prostate tissue may be utilized. A necrosing medicament or agent may be delivered orally, intravenously, systemically, transcutaneously or by other suitable delivery mechanisms. Preferably, the necrosing medicament specifically damages the prostate with little collateral damage or other adverse side effects to other tissue. By way of example, selective apoptotic antineoplastic drugs such as exisulind (APTOSYN or CP 461 may be suitable. Cytoreductive gene therapy may also be employed to medically necrose cancerous prostate tissue. By way of example, herpes simplex virus thymidine kinase gene (HSV-tk) in combination with the prodrug ganciclovir, as described in U.S. Pat. No. 6,217,860 to Woo, et al. may be effective to inhibit DNA polymerase and cause cell death.

In one embodiment of the treatment regimen, the step of necrosing the prostate tissue includes the step of chemically ablating the prostate tissue by injecting ethanol. The devices and procedures described above for injecting ethanol are suitable in the practice of this embodiment of the invention. In the practice of this treatment regimen of the invention, the step of necrosing hyperplastic prostate tissue should be carried out sufficiently to elicit a reparative process in the absence of further treatment. The step of coadministering an antiandrogen is carried out in accordance with the description above regarding timing, suitable antiandrogens, techniques for administration, etc. The step of coadministering a therapeutically effective amount of an antiandrogen may also optionally comprise administering an inhibitor of 5α-reductase, as described above. The step of coadministering a therapeutically effective amount of an antiandrogen may also optionally comprise administering a therapeutically effective amount of an LHRH analogue or LHRH antagonist, as described above.

In another embodiment, the present invention provides a treatment regimen for treating benign prostatic hyperplasia. The treatment regimen includes the steps of damaging hyperplastic prostate tissue sufficiently to elicit a reparative process in the absence of further treatment; and coadministering a therapeutically effective amount of an antiandrogen. The size of the prostate is reduced relative to its size prior to treatment by the treatment regimen.

The step of damaging hyperplastic prostate tissue may be conducted by a variety of surgical and non-surgical techniques. As used herein, the term "damaging" means to cause injury to tissue cells or to a portion of tissue. The term "damaging" includes processes that cause cell or tissue death and processes that do not cause cell or tissue death.

Suitable methods of damaging hyperplastic prostate tissue include irradiation (e.g., with microwave energy, radiofrequency, ultrasound, nuclear radiation, x-rays, or laser ablation), application of heat (thermal ablation), freezing prostate tissue (cryoablation), chemical ablation, surgically damaging prostate tissue, or by electrical vaporization of prostate tissue, among others.

Examples of surgical devices capable of damaging prostate tissue are disclosed in U.S. Pat. No. 4,461,283 to Doi, U.S. Pat. No. 5,672,171 to Andrus, et al. and U.S. Pat. No. 5,630,794 to Lax, et al., and PCT International Publication Nos. WO 92/10142 and WO 93/15664, the entire contents of each of which is herein incorporated by reference. Examples of devices and methods for surgically damaging prostate tissue are disclosed in U.S. Pat. Nos. 5,322,503, 5,562,703, 5,861,002 and 6,231,591, all to Desai, the entire contents of each of which is incorporated by reference.

Also, a medication that induces damage of prostate tissue may be utilized. A damaging medicament or agent may be delivered orally, intravenously, systemically, transcutaneously or by other suitable delivery mechanisms. Preferably, the damaging medicament specifically damages the prostate with little collateral damage or other adverse side effects to other tissue. By way of example, selective apoptotic antineoplastic drugs such as exisulind (APTOSYN) or CP 461 may be suitable. Cytoreductive gene therapy may also be employed to medically damage cancerous prostate tissue. By way of example, introduction of herpes simplex virus thymidine kinase gene (HSV-tk) in combination with the prodrug ganciclovir, as described in U.S. Pat. No. 6,217,860 to Woo, et al. may be effective to inhibit DNA polymerase and cause cell death.

In one embodiment of the treatment regimen, the step of damaging the prostate tissue includes the step of chemically ablating the prostate tissue by injecting ethanol. The devices and procedures described above for injecting ethanol are suitable in the practice of this embodiment of the invention. In the practice of this treatment regimen of the invention, the step of damaging hyperplastic prostate tissue should be carried out sufficiently to elicit a reparative process in the absence of further treatment.

Another embodiment of the present invention also provides a treatment regimen for treating prostate diseases. The treatment regimen of this embodiment includes the steps of injecting an effective amount of ethanol into prostate tissue to ablate a significant amount of prostate tissue; and coadministering a therapeutically effective amount of an antiandrogen. The size of the prostate is reduced relative to its size prior to treatment by the treatment regimen. The treatment regimen is suitable for treatment of prostate tissue diseases including BPH and prostatic carcinoma. The devices and procedures described above for injecting ethanol are suitable in the practice of this embodiment of the invention. By the phrase "significant amount" is meant a measurable change in size of the obstructive prostatic tissue and, in the case of treatment for BPH, an amount such that subsequent alleviation of symptoms of urinary obstruction is achieved. Objective assessment of the effects of therapy may measured by standard methods, including urodynamic flow analysis, transurethral examination, or transrectal ultrasonography, or by an obstructive symptom scoring questionnaire such as the International Prostate Symptom Score (IPSS) or the American Urological Association Symptom Index Score (AUA Score).

Also provided by the present invention is a treatment regimen for treating benign prostatic hyperplasia, including the steps of necrosing hyperplastic prostate tissue by injecting an effective amount of ethanol into a prostate; and coadministering a therapeutically effective amount of an antiandrogen. The size of the prostate is reduced relative to its size prior to treatment by the treatment regimen. The devices and procedures described above for injecting ethanol are suitable in the practice of this embodiment of the invention.

In each of the previously described embodiments, the step of coadministering an antiandrogen is carried out in accordance with the description above regarding timing, suitable antiandrogens, techniques for administration, etc. The step of coadministering a therapeutically effective amount of an antiandrogen may also optionally comprise the step of administering an inhibitor of 5α-reductase, as described above. The step of coadministering a therapeutically effective amount of an antiandrogen may also optionally comprise the step of administering a therapeutically effective amount of an LHRH analogue or LHRH antagonist, as described above.

The present invention further provides a kit for treating a human male. The kit of this embodiment includes a means for necrosing prostate tissue; a therapeutically effective amount of an antiandrogen drug; and a means for administering the antiandrogen drug.

The kit includes a means for necrosing prostate tissue. The means may comprise a surgical device or non-surgical means. Preferably, the means for necrosing prostate tissue comprises a surgical device adapted for delivery of a chemoablation fluid to the prostate tissue. One suitable surgical device is commercially available under the trade name PROSTAJECT from American Medical Systems, Inc. of Minnetonka, Minn. A suitable chemoablation fluid includes, by way of example, ethanol or an injectable gel comprising ethanol.

In one embodiment, the means for necrosing prostate tissue comprises a surgical device for transurethrally delivering a chemoablation fluid such as ethanol to prostate tissue through a needle. The surgical device is preferably sized and shaped for transurethral entry under direct vision. One such surgical device includes a syringe-receiving port for receiving a syringe filled with ethanol or with an antiandrogen in solution, or adapted to receive both fluids. Optionally, a conventional cystoscope and sheath for transurethral entry under direct vision may be utilized as a portion of the kit.

FIGS. 2 and 3 show an embodiment of a suitable surgical device 20 adapted for necrosing prostate tissue by ethanol injection. The structure and operation of the surgical device 20 is described above.

The antiandrogen drug may be any of the non-steroidal or steroidal antiandrogens described above. Bicalutamide (e.g., CASODEX) is one suitable antiandrogen drug for inclusion in the kit.

The means for administering the antiandrogen drug is determined by the manner of delivering the antiandrogen drug. The antiandrogen drug may be provided in tablet form, in oral solution or suspension, in an injectable or intravenous solution or suspension, or in a form for transdermal delivery such as a patch, for example.

Figure 4:
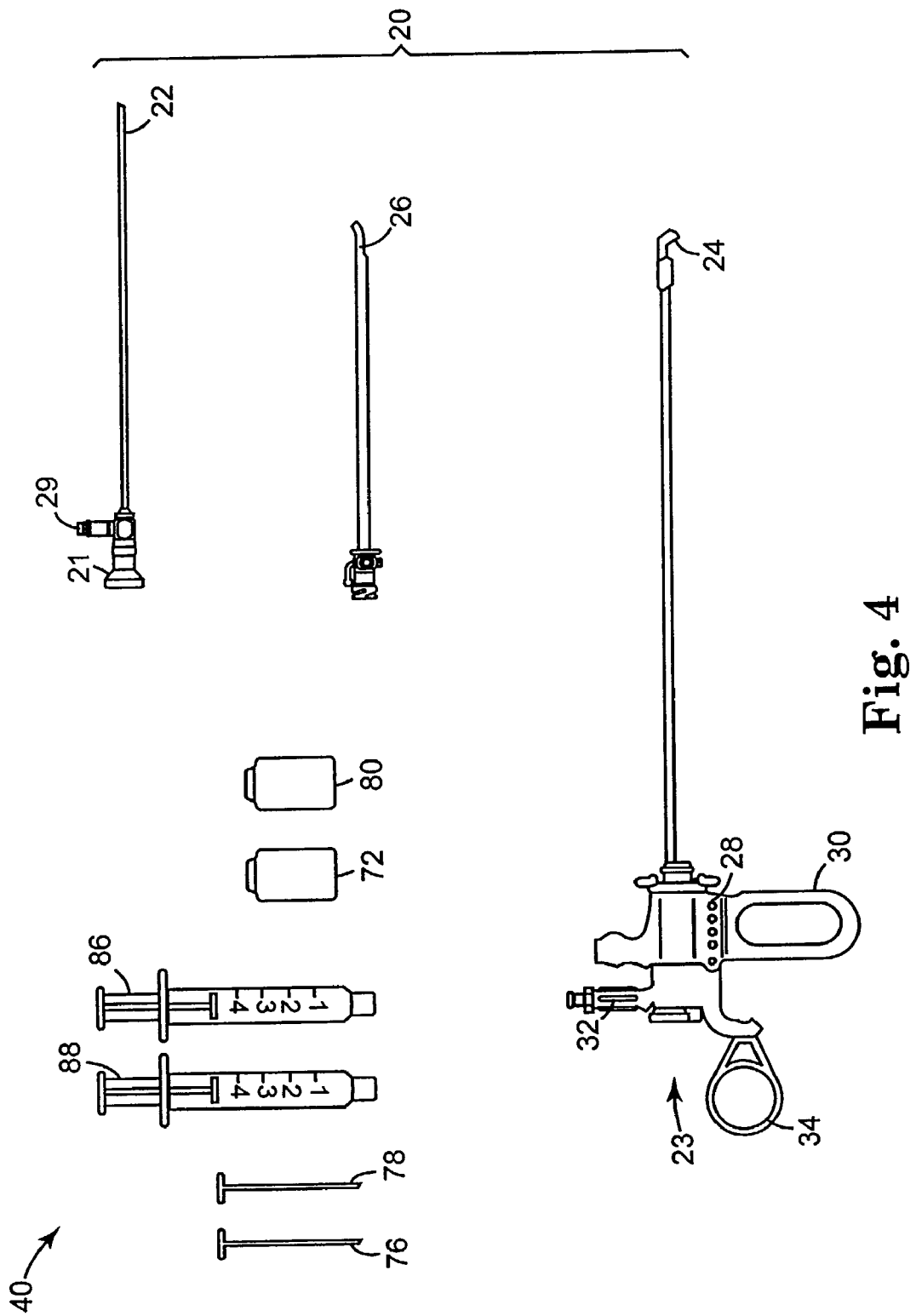
FIG. 4 is a side view showing a surgical kit according to another embodiment of the present invention.

FIG. 4 illustrates one example of a surgical kit according to the present invention. The kit of this embodiment includes a surgical device for necrosing prostate tissue, a therapeutically effective amount of an antiandrogen drug, and a means for administering the antiandrogen drug. The kit 40 includes a surgical device 20 for transurethral delivery of fluids to prostate tissue. Surgical device 20 described and shown in conjunction with FIGS. 2 and 3 is one such device that is suitable for use in the kit 40. The kit 40 also includes a supply or reservoir of ethanol 72 and a supply of an antiandrogen drug 80 in solution or suspension. The ethanol 72 may optionally be provided as an injectable gel. Needles 76, 78 are provided to load the ethanol and antiandrogen, respectively, into syringes 86 and 88 from reservoirs 72 and 80. The syringes 86 and 88 may then be used to deliver the ethanol and antiandrogen drug through the needle 25 (shown in FIG. 3) during a surgical procedure. Alternatively, the antiandrogen drug may be supplied in the kit 40 as an independently injectable treatment that may be conveniently injected at approximately the same time as the ethanol injection, using a needle and syringe (not shown) dedicated for injection of the antiandrogen.

In an alternative embodiment, a kit in accordance with the invention may comprise a non-surgical kit. For example, a non-surgical kit may include a non-surgical medicament for necrosing prostate tissue, and an antiandrogen drug. In this embodiment of a non-surgical kit, the medicament and the antiandrogen drug may be delivered orally (e.g., the medicament and antiandrogen drug may be provided in tablet form), intravenously or in any suitable manner. Depending on the manner of delivery, the kit may also include needles, syringes and reservoirs.

A kit in accordance with the present invention may also comprise both surgical and non-surgical elements. For example, a kit may include a surgical device for necrosing prostate tissue, and non-surgical means for administering the antiandrogen drug, such as an oral tablet.

The elements of the kit may be packaged and sterilized together, or they may be separately packaged and sterilized and assembled into a kit at a later date.

Further, optional treatments may also be incorporated into each embodiment of the kit of the present invention. By way of example, a suspension of an LHRH analogue, and a needle and syringe dedicated for injection of the LHRH analogue, may be included in the kit.

Another embodiment of the present invention provides a kit for treating a human male. The kit of this embodiment includes a first surgical device having a needle for delivering a chemoablation fluid to prostate tissue transurethrally, a therapeutically effective amount of bicalutamide; and a second surgical device for administering bicalutamide.

A reservoir of a chemoablation fluid may optionally be included with the kit of this embodiment. One suitable chemoablation fluid for inclusion in the kit is absolute ethanol, or alternatively, an injectable gel comprising ethanol as described above may be included. Any suitable chemoablation fluid may be included with the kit, however.

In one embodiment, the first surgical device comprises a device for transurethrally delivering ethanol to prostate tissue through a needle. The first surgical device is preferably sized and shaped for transurethral entry under direct vision. One such surgical device includes a syringe-receiving port for receiving a syringe filled with ethanol FIGS. 2 and 3 show surgical device 20, which is a suitable first surgical device, adapted for delivering a chemoablation fluid to prostate tissue. The structure and operation of the surgical device 20 is described above.

The first surgical device may also serve as the second surgical device for administering bicalutamide. Alternatively, a separate surgical device may be included as the second surgical device for administering bicalutamide. For example, bicalutamide may be provided as an injectable solution, and the second surgical device may comprise a dedicated needle and syringe for injection of bicalutamide. The second surgical device may be adapted for administration of bicalutarnide transurethrally, perineally, percutaneously, transdermally, or by any effective manner.

The present invention also provides for the use of both an antiandrogen and ethanol for the manufacture of a combination medicament for the treatment of benign prostatic hyperplasia or prostatic carcinoma. The combination medicament is useful in the practice of the treatment regimens of the present invention. In particular, the ethanol is intended to be used as an ablating or necrosing agent, and the antiandrogen is intended to be coadministered according to any of the treatment regimens described above. The antiandrogens described above are suitable for the combination medicament. Bicalutamide in particular is a suitable non-steroidal antiandrogen.

The following Example demonstrates the efficacy of a treatment regimen in accordance with an embodiment of the present invention.

EXAMPLE

Human patients exhibiting symptoms of BPH were treated by transurethral ethanol ablation of prostate tissue, with coadministration of the antiandrogen bicalutamide. The treatments for selected patients are summarized in Table 1. Measurements of each patient's prostate size were obtained prior to ethanol ablation by MRI. Flowmetry measurements were also taken. Maximum flow rate ($Q_{max}$) and median flow rate ($Q_{med}$) are given in Table 2.

Each patient was then administered ethanol ablation therapy by transurethral injection directly into prostate tissue, as summarized in Table 1. Total amount of ethanol injected ranged from about 22% to about 38% relative to the volume of the patient's prostate. The number of injection sites ranged from 3 to 11; the average number of injection sites was 5.8. Following ethanol ablation therapy, each patient was administered bicalutamide, 150 mg orally each day for sixty days, beginning on the day of treatment.

TABLE 1

Summary of ethanol ablation therapy for individual patients.

| Patient No. | Prostate Size (g) | Injection Sites | Volume of Ethanol (mL) |
|---|---|---|---|
| 1 | 115 | 6 | 26 |
| 3 | 75 | 4 | 20 |
| 4 | 112 | 6 | 25 |
| 7 | 80 | 6 | 30 |
| 9 | 40 | 5 | 15 |
| 10 | 51 | 3 | 15 |
| 11 | 56 | 5 | 21 |
| 12 | 164 | 8 | 36 |
| 14 | 91 | 7 | 31 |
| 15 | 34 | 3 | 12 |
| 16 | 125 | 7 | 36 |
| 17 | 48 | 4 | 17 |
| 18 | 96 | 6 | 30 |
| 19 | 105 | 6 | 35 |
| 20 | 175 | 11 | 50 |

A three-month and six-month follow-up examination was done for each patient to evaluate prostate size and flowmetry results. The data given in Table 2 demonstrates that reductions in prostate size of more than 50% are achievable by the practice of one embodiment of the present invention. Relief from symptoms such as urinary retention is also demonstrated for patients having oversized prostates (i.e., prostate mass greater than 80 g).

Survey data was also acquired pre-treatment and at the three-month and six-month followups. Patients were evaluated for subjective symptom severity using an International Prostate Symptom Score questionnaire. Results are given in Table 3. The data indicates that relief of the symptoms of BPH is achieved in nearly every case.

TABLE 3

Relief of symptoms.

| Patient No. | Pre-treatment IPPS* | IPSS at 3 months | IPSS at 6 months |
|---|---|---|---|
| 1 | (retention) | 3 | 3 |
| 3 | (retention) | 20 | 20 |
| 4 | (retention) | 4 | 4 |
| 7 | 20 | 18 | 8 |
| 9 | (retention) | 10 | 9 |
| 10 | 22 | 4 | 6 |
| 11 | 16 | 8 | 8 |
| 12 | (retention) | 24 | 14 |
| 14 | 20 | 9 | 8 |
| 15 | 26 | 21 | 8 |
| 16 | 23 | 14 | 12 |
| 17 | (retention) | 8 | 7 |
| 18 | 20 | 15 | 12 |
| 19 | (retention) | 10 | 9 |
| 20 | 27 | 13 | 10 |

*"(retention)" indicates absence of flow, with no IPSS score assigned.

This invention may take on various modifications and alterations without departing from the spirit and scope thereof. Accordingly, it is to be understood that this invention is not to be limited to the above-described, but it is to be controlled by the limitations set forth in the following claims and any equivalents thereof. It is also to be understood that this invention may be suitably practiced in the absence of any element not specifically disclosed herein.

In describing preferred embodiments of the invention, specific terminology is used for the sake of clarity. The invention, however, is not intended to be limited to the specific terms so selected, and it is to be understood that each term so selected includes all equivalents that operate similarly.

TABLE 2

Reduction in prostate mass and change in symptoms.

| | Pre-treatment | | | Post-treatment Evaluation (3 months) | | | Post-treatment Evaluation (6 months) | | |
|---|---|---|---|---|---|---|---|---|---|
| Patient No. | Size (g) | $Q_{max}$ (mL/sec) | $Q_{med}$ (mL/sec) | Size (g) | $Q_{max}$ (mL/sec) | $Q_{med}$ (mL/sec) | Size (g) | $Q_{max}$ (mL/sec) | $Q_{med}$ (mL/sec) |
| 1 | 115 | 0 | 0 | 40 | 21 | 9 | 21 | 21 | 9 |
| 3 | 75 | 0 | 0 | 15 | 17 | 5 | 19 | 17 | 5 |
| 4 | 112 | 0 | 0 | 40 | 18 | 11 | 28 | 18 | 11 |
| 7 | 80 | 8 | 4 | 36 | 7 | 3 | 30 | 13 | 10 |
| 9 | 40 | 0 | 0 | 28 | 4 | 3 | 20 | 19 | 11 |
| 10 | 51 | 7 | 4 | 30 | 12 | 4 | 21 | 15 | 9 |
| 11 | 56 | 11 | 7 | 25 | 11 | 7 | 20 | 14 | 9 |
| 12 | 164 | 0 | 0 | 78 | 17 | 5 | 19 | 30 | 13 |
| 14 | 91 | 11 | 5 | 78 | 13 | 7 | 32 | 15 | 10 |
| 15 | 34 | 9 | 5 | 30 | 12 | 7 | 28 | 13 | 9 |
| 16 | 125 | 8 | 3 | 63 | 18 | 7 | 18 | 15 | 9 |
| 17 | 48 | 0 | 0 | 45 | 11 | 5 | 20 | 15 | 10 |
| 18 | 96 | 7 | 6 | 42 | 15 | 8 | 18 | 17 | 10 |
| 19 | 105 | 0 | 0 | 54 | 10 | 2 | 27 | 12 | 8 |
| 20 | 175 | 7 | 5 | 98 | 13 | 2 | 23 | 20 | 11 |

What is claimed is:

1. A treatment regimen for treating benign prostatic hyperplasia comprising:
   a) necrosing hyperplastic prostate tissue sufficiently to elicit a reparative process, wherein necrosing prostate tissue includes surgically damaging a portion of prostate tissue by injecting ethanol into the portion of prostate tissue; and
   b) coadministering a therapeutically effective amount of an antiandrogen;

such that steps a) and b) are sufficient to reduce the size of the prostate relative to its size prior to treatment.

2. The treatment regimen of claim 1 wherein surgically damaging the prostate tissue further includes heating the portion of prostate tissue.

3. The treatment regimen of claim 1 wherein surgically damaging the prostate tissue further includes cryoablating the portion of prostate tissue.

4. The treatment regimen of claim 1 wherein surgically damaging the prostate tissue futher includes irradiating the portion of prostate tissue with electromagnetic radiation.

5. The treatment regimen of claim 1 wherein surgically damaging the prostate tissue further includes irradiating the portion of prostate tissue with nuclear radiation.

6. The treatment regimen of claim 1 wherein surgically damaging the prostate tissue futher includes electrically vaporizing the portion of prostate tissue.

7. The treatment regimen of claim 1 wherein necrosing prostate tissue further includes chemically ablating a portion of prostate tissue.

8. The treatment regimen of claim 1 wherein ethanol is injected transurethrally.

9. The treatment regimen of claim 1 wherein ethanol is injected in the form of an injectable gel.

10. The treatment regimen of claim 1 wherein necrosing prostate tissue further includes medicinally damaging a portion of prostate tissue.

11. The treatment regimen of claim 1 wherein coadministering an antiandrogen includes administering a non-steroidal antiandrogen.

12. The treatment regimen of claim 11 wherein the non-steroidal antiandrogen is selected from the group consisting of flutamide, nilutamide and bicalutamide.

13. The treatment regimen of claim 11 wherein the non-steroidal antiandrogen comprises bicalutamide.

14. The treatment regimen of claim 1 wherein coadministering an antiandrogen includes administering a steroidal antiandrogen.

15. The treatment regimen of claim 14 wherein the steroidal antiandrogen is selected from the group consisting of cyproterone acetate, megestrol acetate, medroxyprogesterone acetate, chlormadinone acetate, and WIN 49596.

16. The treatment regimen of claim 1 wherein coadministering an antiandrogen occurs after necrosing the prostate tissue.

17. The treatment regimen of claim 1 wherein at least part of the step of coadministering an antiandrogen occurs prior to necrosing the prostate tissue.

18. The treatment regimen of claim 1 wherein at least part of the step of coadministering an antiandrogen occurs substantially during the step of necrosing the prostate tissue.

19. The treatment regimen of claim 1 wherein coadministering an antiandrogen further includes administering a luteinizing hormone-releasing hormone analog.

20. The treatment regimen of claim 19 wherein the luteinizing hormone-releasing hormone analog is selected from the group consisting of leuprolide acetate, goserelin acetate, buserelin acetate, and triptorelin pamoate.

21. The treatment regimen of claim 1 wherein coadministering an antiandrogen further includes administering a luteinizing hormone-releasing hormone antagonist.

22. The treatment regimen of claim 21 wherein the luteinizing hormone-releasing hormone antagonist is selected from the group consisting of cetrorelix and abarelix.

23. The treatment regimen of claim 1 wherein coadministering an antiandrogen further includes administering an inhibitor of 5α-reductase.

24. The treatment regimen of claim 23 wherein the inhibitor of 5α-reductase effectively inhibits Type II 5α-reductase.

25. The treatment regimen of claim 23 wherein coadministering an inhibitor of 5α-reductase includes administering a synthetic 4-azasteroid compound.

26. The treatment regimen of claim 25 wherein the 4-azasteroid compound is selected from finasteride, dutasteride and PNU 157706.

27. A treatment regimen for treating benign prostatic hyperplasia comprising:
   a) damaging hyperplastic prostate tissue sufficiently to elicit a reparative process, wherein damaging prostate tissue includes chemically ablating a portion of prostate tissue by injecting ethanol into the portion of prostate tissue; and
   b) coadministering a therapeutically effective amount of an antiandrogen;

such that steps a) and b) are sufficient to reduce the size of the prostate relative to its size prior to treatment.

28. The treatment regimen of claim 27 wherein damaging prostate tissue further includes surgically damaging a portion of prostate tissue.

29. The treatment regimen of claim 27 wherein ethanol is injected transurethrally.

30. The treatment regimen of claim 27 wherein ethanol is injected in the form of an injectable gel.

31. The treatment regimen of claim 27 wherein damaging prostate tissue further includes medicinally damaging a portion of prostate tissue.

32. The treatment regimen of claim 27 wherein coadministering an antiandrogen includes administering a non-steroidal antiandrogen.

33. The treatment regimen of claim 32 wherein the non-steroidal antiandrogen is selected from the group consisting of flutamide, nilutamide and bicalutamide.

34. The treatment regimen of claim 32 wherein the non-steroidal antiandrogen comprises bicalutamide.

35. The treatment regimen of claim 27 wherein coadministering an antiandrogen includes administering a steroidal antiandrogen.

36. The treatment regimen of claim 35 wherein the steroidal antiandrogen is selected from the group consisting of cyproterone acetate, megestrol acetate, medroxyprogesterone acetate, chlormadinone acetate, and WIN 49596.

37. A treatment regimen for treating benign prostatic hyperplasia comprising:
   a) necrosing hyperplastic prostate tissue by injecting an effective amount of ethanol into a prostate; and
   b) coadministering a therapeutically effective amount of an antiandrogen;

such that steps a) and b) are sufficient to reduce the size of the prostate relative to its size prior to treatment.

38. The treatment regimen of claim 37 wherein ethanol is injected transurethrally.

39. The treatment regimen of claim 37 wherein ethanol is injected in the form of an injectable gel.

40. The treatment regimen of claim 37 wherein the antiandrogen comprises bicalutamide.

* * * * *